(12) United States Patent
Goto

(10) Patent No.: US 8,715,164 B2
(45) Date of Patent: May 6, 2014

(54) ENDOSCOPIC INCISION SYSTEM

(75) Inventor: Hiroaki Goto, Tokyo (JP)

(73) Assignee: Olympus Medical Systems Corp. (JP)

( * ) Notice: Subject to any disclaimer, the term of this patent is extended or adjusted under 35 U.S.C. 154(b) by 461 days.

(21) Appl. No.: 12/323,716

(22) Filed: Nov. 26, 2008

(65) Prior Publication Data

US 2009/0177030 A1    Jul. 9, 2009

(30) Foreign Application Priority Data

Nov. 28, 2007    (JP) .................................. 2007-307688

(51) Int. Cl.
  *A61B 1/00*    (2006.01)
(52) U.S. Cl.
  USPC ........... 600/104; 600/121; 600/123; 600/127; 600/129; 600/183; 606/32; 606/37; 606/39; 606/46
(58) Field of Classification Search
  USPC ................. 600/104, 183, 121, 123, 127, 129; 604/104–109; 606/32–52, 180, 190, 606/198
  See application file for complete search history.

(56) References Cited

U.S. PATENT DOCUMENTS

| | | | | |
|---|---|---|---|---|
| 5,415,656 | A |  | 5/1995 | Tihon et al. ........................ 606/46 |
| 6,196,966 | B1 | * | 3/2001 | Kerin et al. ....................... 600/104 |
| 7,101,378 | B2 |  | 9/2006 | Salameh et al. .................. 606/113 |
| 7,192,430 | B2 | * | 3/2007 | Truckai et al. ..................... 606/46 |
| 7,291,146 | B2 | * | 11/2007 | Steinke et al. ..................... 606/41 |
| 7,485,092 | B1 | * | 2/2009 | Stewart et al. ................... 600/127 |
| 2005/0049454 | A1 | * | 3/2005 | Ouchi ............................ 600/105 |
| 2005/0096647 | A1 | * | 5/2005 | Steinke et al. ..................... 606/41 |
| 2007/0083081 | A1 | * | 4/2007 | Schlagenhauf et al. ....... 600/104 |
| 2007/0112341 | A1 | * | 5/2007 | Edwards et al. .................. 606/41 |
| 2007/0213702 | A1 | * | 9/2007 | Kogasaka et al. ................ 606/32 |
| 2007/0260273 | A1 | * | 11/2007 | Cropper et al. ................ 606/185 |

FOREIGN PATENT DOCUMENTS

| | | |
|---|---|---|
| EP | 1 808 134 | 7/2007 |
| EP | 1 854 421 | 11/2007 |
| JP | 57-90117 | 6/1982 |
| JP | 62-122651 | 6/1987 |
| JP | 8-509894 | 10/1996 |

(Continued)

OTHER PUBLICATIONS

Extended European Search Report dated Dec. 7, 2009 in corresponding European Patent Application No. EP 08 02 0749 (in English language).

(Continued)

*Primary Examiner* — Matthew J Kasztejna
*Assistant Examiner* — Kevin G Barry, III
(74) *Attorney, Agent, or Firm* — Ostrolenk Faber LLP

(57) ABSTRACT

An endoscopic incision system includes: an endoscope; a cylindrical member for covering at least a distal end of an insertion section of the endoscope; and at least an incision section for incising a living tissue, the incision section being provided to a distal end of the cylindrical member and being capable of being exposed from the distal end of the cylindrical member outwardly. In this configuration, the radially expanding incision section will not be twisted or bent, and the incision section prevented from inadvertent fall-off can maintain the desirable shape when it is operated and rotated.

4 Claims, 6 Drawing Sheets

(56) References Cited

FOREIGN PATENT DOCUMENTS

| JP | 2001-517962 | 10/2001 |
|----|-------------|---------|
| JP | 2001-321389 | 11/2001 |
| JP | 2002-301088 | 10/2002 |
| JP | 2004-73582  | 3/2004  |
| JP | 2005-066138 | 3/2005  |
| WO | WO 97/13451 | 4/1997  |

OTHER PUBLICATIONS

Japanese Office Action mailed Jul. 10, 2012 in connection with corresponding Japanese Patent Application No. 2007-307688 and English translation thereof.

Japanese Office Action mailed Mar. 12, 2013 in connection with corresponding Japanese Patent Application No. 2007-307688 and English translation thereof.

* cited by examiner

ENDOSCOPIC INCISION SYSTEM

The present application is based on patent application No. 2007-307688 filed in Japan Nov. 28, 2007, the content of which is incorporated herein by reference.

BACKGROUND OF THE INVENTION

1. Field of the Invention

The present invention relates to an endoscopic incision system combined with an overtube, an endoscopic-use cap, or the like, that covers an endoscope and the insertion section of the endoscope.

2. Background Art

Conventionally known instruments for incising, for example, a living tissue for use with endoscopes normally accommodates a wire forming a knife section in a flexible sheath or disposes the wire along the outer periphery of the circumferential wall of the flexible sheath, and an operator expands a part of the wire outwardly relative to the flexible sheath when the living tissue is actually incised. The living tissue in this state is incised by compressing the expanded part of the wire to a predetermined site of the living tissue which is supposed to be incised while applying a high-frequency electric current to the wire (See, for example, Japanese Unexamined Patent Application Publication (Translation of PCT Application) No. H8-509894 and Japanese Unexamined Patent Application, First Publication No. 2004-73582).

SUMMARY OF THE INVENTION

An object of the present invention is to provide an endoscopic incision system capable of maintaining a desirable shape of an incision section that is free from twists, bends, and prevents the inadvertent fall of the incision section upon being operated for rotation.

The present invention adopts the following measures.

An endoscopic incision system according to the present invention includes: an endoscope; a cylindrical member for covering at least a distal end of an insertion section of the endoscope; and at least an incision section for incising a living tissue wherein the incision section is provided to a distal end of the cylindrical member and is capable of being exposed from the distal end of the cylindrical member outwardly.

The present endoscopic incision system does not have to change the shape of the incision section when it is used for incision. Therefore, the incision section will not be twisted or bent during incision by presetting the incision section to have a higher stiffness. In addition, the incision section resistant to inadvertent fall-off can maintain the desirable shape when it is operated and rotated.

It is preferable that a dome-shaped or round-tip distal end section be provided in the center of the distal end of the cylindrical member in the endoscopic incision system according to the present invention.

In this case of insertion of the distal end of the cylindrical member of the endoscopic incision system into a narrow section of a living tissue such as a stricture section in an esophagus while observing with the endoscope, the cylindrical member or the insertion section of the distal end section can be extended while distally extending the distal end section having the dope-shape, round-tip shape or the like and provided to the center of the distal end of the cylindrical member.

It is preferable that a dome-shaped or round-tip bougie section is provided in a center of the distal end of the cylindrical member in the endoscopic incision system according to the present invention.

In the case of insertion of the distal end of the cylindrical member of the endoscopic incision system into a narrow section of a living tissue such as a stricture section in an esophagus while observing the distal end of the cylindrical member of the endoscopic incision system, the bougie section having the dome-shape, or round-tip shape or the like and provided to the center of the distal end of the cylindrical member can immediately expand the living tissue free from damage can be set at a predetermined position.

It is preferable that the incision section is a linear member or a sheet member radially expanding outward while proximally extending from the bougie section in the endoscopic incision system according to the present invention.

In this case, using the bougie section to insert and set the distal end of the cylindrical member of the endoscopic incision system at a narrow point of the living tissue such as the stricture section or the like in the esophagus and subsequently rotating the cylindrical member allow the living tissue to be incised immediately.

In addition, the incision section formed continuously to the proximal end of the bougie section allows the living tissue to be expanded by the bougie section and incised by the incision section continuously, thereby facilitating operations.

It is preferable that the cylindrical member be an overtube covering the insertion section of the endoscope in the endoscopic incision system according to the present invention.

In this case, rotating the overtube allows the distally-located incision section to incise a predetermined section of the living tissue.

It is preferable that the cylindrical member be a cap attached to the distal end section of the insertion section of the endoscope in the endoscopic incision system according to the present invention.

In this case, rotating the insertion section of the endoscope allows the incision section provided to the distal end of the cap attached to the distal end of the insertion section to incise a predetermined section of the living tissue.

It is preferable that the cap be transparent in the endoscopic incision system according to the present invention.

In this case, the cap attached to the distal end of the endoscope is free from obstructing the visual field in the endoscope and does not hinder maneuvers of the endoscope.

It is preferable that a recessed section or a hollow section be formed inward relative to the incision section of the cap in the endoscopic incision system according to the present invention.

In this case, the living tissue can be incised while the living tissue is captured in the recessed section or the hollow section formed inward relative to the incision section of the cap. Accordingly, deeper incising operation can be facilitated.

It is preferable that the incision section is a conductive wire to which a high-frequency electric current is supplied in the endoscopic incision system according to the present invention.

The conductive wire in this case may be usable as a cutting knife.

It is preferable that the bougie section be an insulator member in the endoscopic incision system according to the present invention.

It is possible to prevent the incision section from inadvertently incising a tissue making contact with the bougie section when a high-frequency electric current is supplied and discharged to the incision section that is operated as a cutting knife.

The present invention does not have to change the shape of incision section whether or not it is used for incision. Therefore, the incision section will not be twisted or bent during incision by presetting the incision section to have a higher stiffness. In addition, the incision section which prevents inadvertent fall-off can maintain a desirable shape when it is operated and rotated.

PREFERRED EMBODIMENTS

First Embodiment

Figure 1:
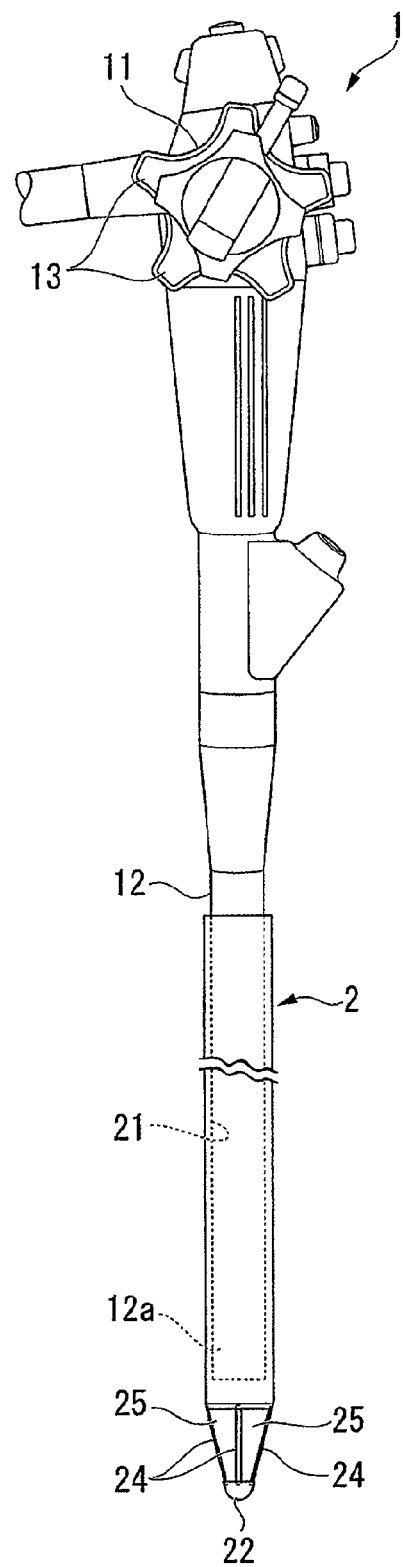
FIG. 1 is a front elevation showing an endoscopic incision system according to a first embodiment of the present invention.
Figure 2:
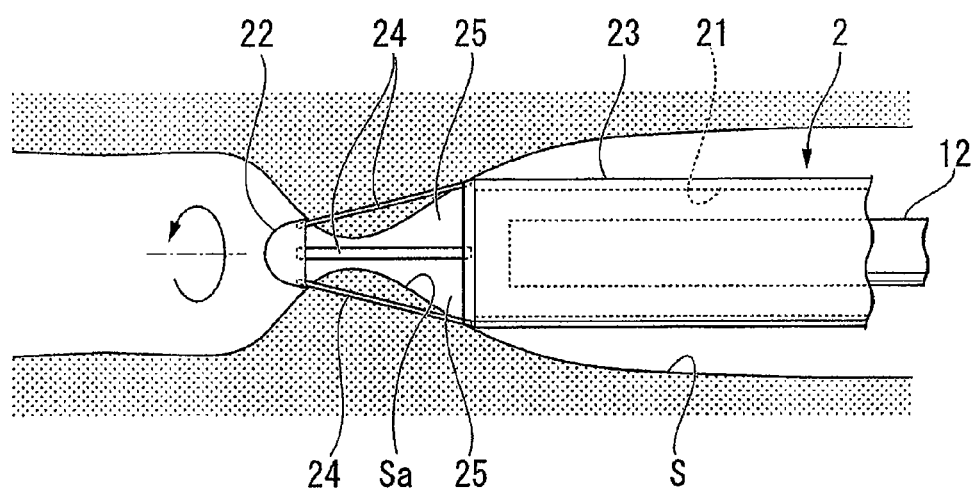
FIG. 2 is a side view showing the distal end section of the endoscopic incision system.

FIGS. 1 and 2 show an endoscopic incision system according to a first embodiment of the present invention. FIG. 1 is an general isometric view showing the endoscopic incision system having an overtube covering the outer periphery of an insertion section of an endoscope. FIG. 2 is a side view showing the distal end section of the endoscopic incision system for incising the stricture section of an esophagus.

The endoscopic incision system according to the present embodiment is provided with: an endoscope 1; and an overtube (cylindrical member) 2 that covers the outer periphery of an insertion section 12 of the endoscope 1.

As shown in FIG. 1, the endoscope 1 is a flexible endoscope having the elongated flexible insertion section 12 extending from an operation section 11 provided on the endoscope 1 which is to be operated by an operator.

A distal end section 12a of the insertion section 12 can be bent by operating an angle knob 13 disposed on the operation section 11. Provided on the distal end section 12a are: an object lens; the distal end surface of an optical fiber for transmitting light from an externally-installed light source apparatus; and the distal end opening of a channel. (These components are not shown in the drawings.) The channel is a conduit that is connected to an insufflation apparatus, a liquid-supply apparatus, or a suction apparatus that is disposed externally, via a universal cable, and that is employed to supply and evacuate liquid to and from the body.

In this embodiment, a position where the operation section 11 with respect to the endoscope 1 and an overtube 2 indicates a proximal side, and the reverse side indicates a distal side.

The flexible overtube 2 capable of deforming in accordance with the insertion section 12 of the endoscope has a lumen 21 thereinside that allows the insertion section 12 of the endoscope 1 to freely extend or retract therethrough. The proximal end of the lumen 21 has an opening into which the insertion section 12 of the endoscope 1 is inserted.

A bougie section 22 having a dome-shape is provided in the center of the distal end of the overtube 2. The bougie section 22 expands a stricture section which reduces the size of a body cavity when the overtube 2 is inserted into a hollow organ, an abdominal cavity, an esophagus, or the like of a patient (object).

A plurality of linear members (incision section) 24 such as wires (four pieces in an example shown in FIG. 2), disposed at intervals in the circumferential direction, are disposed between the bougie section 22 and a tube main unit 23 of the overtube 2. The linear members 24 radially expand outward while extending from the bougie section 22 to the proximal end. Spaces 25 are formed among the linear members 24. It should be noted that the linear members 24 are not limited to four pieces; and the linear members 24 may be in a single piece, two pieces, three pieces, five pieces or more.

The plurality of linear members 24 combine a function of supporting the bougie section 22 formed on the distal end and a function of blades for incising a living tissue such as the stricture section in the esophagus when the overtube 2 is rotated around the axial line thereof in the body cavity such as the esophagus.

A maneuver using the endoscopic incision system having the aforementioned configuration for incising the stricture section in the esophagus will be explained next.

As shown in FIG. 1, in the beginning, the insertion section 12 of the endoscope 1 is covered by the overtube 2. Subsequently, the insertion section 12 of the endoscope 1 covered by the overtube 2 is inserted into a mouth and introduced into a eshophagus S, and then, the stricture section Sa is observed based on an endoscopically-obtained image as shown in FIG. 2. Upon acknowledging the location of the stricture section Sa, the linear members 24 provided to the distal end section of the overtube 2 are disposed to oppose to the stricture section Sa.

The overtube 2 in this case can be moved smoothly and deeply into the body cavity since the bougie section 22 compressing the stricture section Sa outward without damaging the surficial part thereof can expand the eshophagus S even though the overtube 2 is extended into the stricture section Sa protruding inwardly in the eshophagus S or the esophagus S is blocked.

Subsequently, the proximal end of the overtube 2 is rotated around the axial line thereof while making sure, based on the endoscopilcally-obtained image, that the linear members 24 provided to the distal end section of the overtube 2 are maintained to oppose the stricture section Sa in the esophagus S. The rotation of the overtube 2 transmitted from the proximal end to the distal end thereof causes the distally-located linear members 24 to rotate uniformly. The rotation of the linear members 24 enables the incising of the living tissue such as the stricture section Sa or the like in the esophagus S.

The incision sections of the linear members 24 in this case do not have to change their shapes even if it is used for incision. Accordingly, the linear members 24 can be preset to have higher stiffness. This results in allowing the linear members 24 to maintain their desirable shapes because the linear members 24 are free from twist or bend during incision and prevent inadvertent falloff upon being rotated.

In addition, the overtube 2 upon being extended into the body cavity causes the living tissue to enter the space 25 because the linear members 24 are disposed to expand outward radially while extending from the bougie section 22 to the proximal end, and because the space 25 is formed among the linear members 24.

Wires used in conventional instruments that expand the wires radially for incision must have low stiffness that allows wires to be freely deformable because the shape of each wire must be variable based on whether or not an incision is conducted. Consequently, such a configuration incapable of assuring stable orientation control during incision was disadvantageous because the wires, which might inevitably twist or bend upon being expanded partly in radial direction to a significant degree, could not be radially expanded into a desirable shape.

In particular, an operation including the rotation of the wires which was susceptible to the fall of wires might result in an incomplete maneuver.

According to the first embodiment of the present invention, an operation of incising a living tissue such as a stricture section Sa by means of linear members 24 can be facilitated since a desirable shape of linear members 24 can be maintained during incision. In addition, the linear members 24 capable of capturing the living tissue into the space 25 formed among the linear members 24 facilitate operation during incision and enable a deeper incision.

The overtube 2 may be removed together with the insertion section 12 of the endoscope 1 from the body after incision.

It should be noted that the insertion section 12 of the overtube 2 of the high-frequency electric current terminal may be inserted into the body cavity while a shift of the insertion section 12 relative to the overtube 2 in the longitudinal direction is regulated by a fixture section provided between the insertion section 12 and the overtube 2.

The function of the linear members 24 in the first embodiment is not limited to cutting blades, and the linear members 24 may be so-called high-frequency knives for incision use of living tissue by discharging a high-frequency electric current to the linear members 24. In this case, the linear members 24 must be made of a conductive material.

Also, the bougie section 22 may be formed by a transparent material for obtaining good visual field in the endoscope.

Second Embodiment

Figure 3:
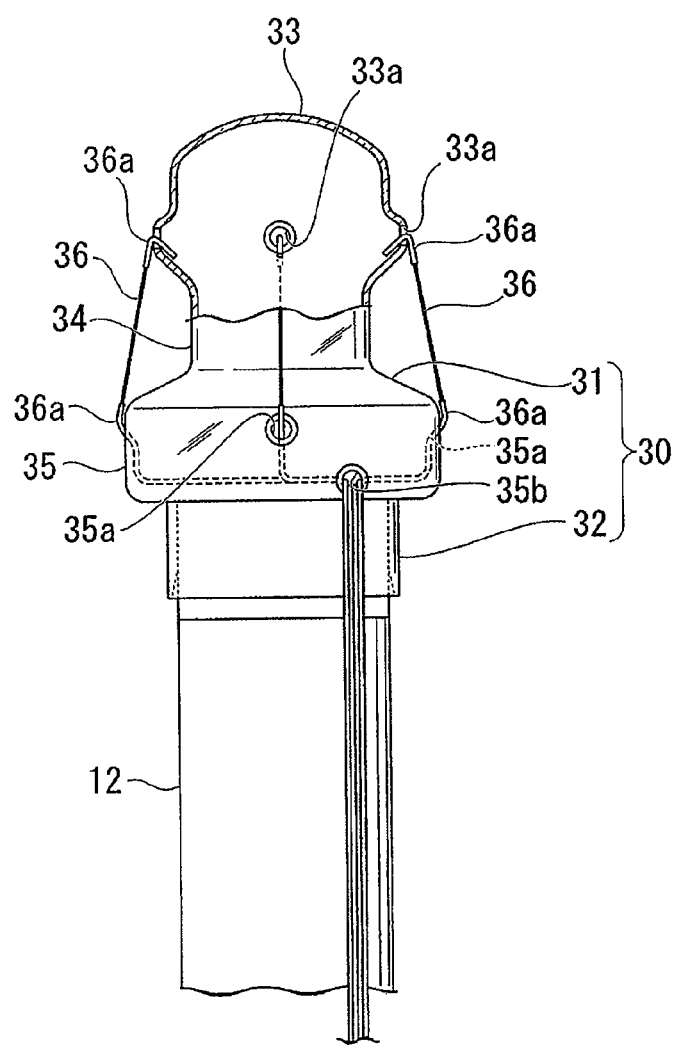
FIG. 3 is a fragmentary sectional view of the main part of the endoscopic incision system according to a second embodiment of the present invention.

FIG. 3 shows the main part of an endoscopic incision system according to a second embodiment of the present invention.

The feature of the second embodiment is the use of a cap 30 that is a cylindrical member for covering the distal end of an insertion section of an endoscope. It should be noted that configurations that are similar to those of the first embodiment will be assigned the same numeric symbols and redundant explanations thereof will be omitted.

That is, as shown in FIG. 3, the cap 30 attached to the distal end of the insertion section 12 of the endoscope covers the distal end of the insertion section.

The cap 30 is formed by a distally-located cap main unit 31 and a cylindrical connection section 32 for attaching the cap main unit 31 to the distal end of the insertion section of the endoscope.

The cap main unit 31 made of a transparent insulative engineering plastics material has a bougie section 33, the radially-expanded section 35, and a ring groove section (recessed section) 34. The bougie section 33 provided to the distal end of the cap main unit 31 has a dome shape. The radially-expanded section 35 is provided to the proximal end of the cap main unit 31. The ring groove section 34 is formed between the bougie section 33 and the radially-expanded section 35.

The proximal end of the bougie section 33 is set to have an outer diameter that is substantially the same as that of the insertion section 12 of the endoscope or greater in some degree. The outer diameter of a bottom section of the ring groove section 34 is set to be smaller than the outer diameter of the insertion section 12 of the endoscope. The radially-expanded section 35 is set to have an outer diameter greater than that of the insertion section 12 of the endoscope.

A plurality of linear members 36 such as wires (FIG. 3 shows four pieces of wire) attached between the bougie section 33 and the radially-expanded section 35 and exposed outwardly are disposed at intervals in the circumferential direction. In addition, the linear members 36 extending from the bougie section 33 to the radially-expanded section 35 expand radially outward. The distal end of each linear member 36 is inserted into a hole 33a formed on the bougie section 33 from outside to inside. The proximal end of each linear member 36 is inserted into a hole 35a formed on the distal end of the radially-expanded section 35 from outside to inside. The proximal ends of the linear members 36 are gathered in the radially-expanded section 35 and extracted outwardly from a single hole 35b formed on the proximal end of the radially-expanded section 35. Subsequently, the extracted proximal ends are passed thereoutside in the longitudinal direction of the insertion section 12 of the endoscope, and then connected to a high-frequency electric current terminal, which is not shown in the drawings.

Coating layers 36a are provided on the outer peripheries of the linear members 36 excluding the exposed part in order to prevent a plastic cap main unit 31 or a rubber-made connection section 32, which will be explained later, from being damaged by heat which will be transferred from the linear members 36 producing a significant amount of heat when a high-frequency electric current is discharged thereto.

It should be noted that the linear members 36 do not have to be connected to high-frequency electric current terminals separately. For example, the linear members 36 while extending from the cap 30 to the insertion section 12 may be bundled together, or the linear members 36 may be connected to a wire which is electrically connected to a high-frequency electric current terminal. In addition, the linear members 36 or the wire that is connected to the high-frequency electric current terminal do not have to pass through in the exterior of the insertion section 12 of the endoscope. For example, the linear members 36 or the wire may be provided in a channel passing through the insertion section 12 of the endoscope and connected to a high-frequency electric current terminal.

In addition, the connection section 32 made of an elastically deformable material, for example, rubber or the like and attached to the distal end of the insertion section 12 of the endoscope by utilizing its elasticity is incapable of rotating around the axial line thereof. It should be noted that the connection section 32 does not have to have a structure that can engage with the insertion section 12 of the endoscope by utilizing its elasticity. For example, the connection section 32 incapable or freely rotating may be attached to the distal end of the insertion section 12 of the endoscope by means of a screw or an engagement using recess and projection or the like.

The endoscopic incision system according to the second embodiment disposes the linear members 36 attached to the cap 30 to be opposed to, for example, a stricture section Sa developed in an esophagus and rotates the insertion section 12 of the endoscope in this state around the axial line thereof. Simultaneously, a high-frequency electric current is supplied to the linear members 36. Accordingly, the linear members 36 which are rotatable unitarily with the cap 30 and use heat produced by the high-frequency electric current can incise the living tissue of the stricture section Sa in the esophagus.

In addition, the endoscopic incision system according to the second embodiment can facilitate operations for deeply incising the living tissue, for example, the stricture section Sa or the like by means of each linear member 36 since a ring groove section 34 is provided inwardly relative to the linear members 36 of the cap main unit 31, and since the living tissue which is supposed to be incised is captured reliably.

Third Embodiment

Figure 4:
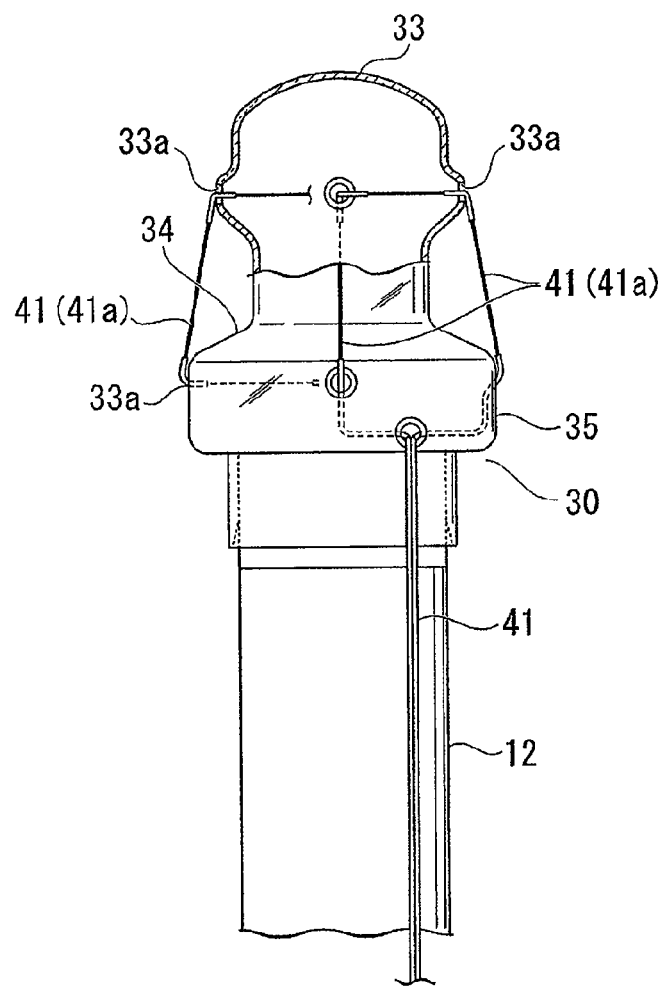
FIG. 4 is a fragmentary sectional side view of the main part of the endoscopic incision system according to a third embodiment of the present invention.
Figure 5:
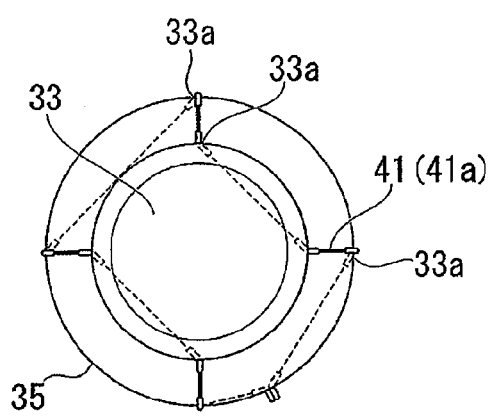
FIG. 5 is a front view of the main part of the endoscopic incision system according to the third embodiment of the present invention.

FIGS. 4 and 5 show the main part of an endoscopic incision system according to a third embodiment of the present invention. FIG. 4 is a cutaway view showing the cross-section of the main part. FIG. 5 is a plan view of the main part. It should be noted that configurations that are similar to those of the previously explained second embodiment will be assigned the same numeric symbol and redundant explanation thereof will be omitted.

The third embodiment is different from the second embodiment because a linear member 41 provided between a bougie section 33 and the radially-expanded section 35 is in one piece in place of the plurality of linear members.

That is, a plurality of holes 33a are provided at intervals in the circumferential direction between the proximal end section of the bougie section 33 and the distal end section of the radially-expanded section 35 while the ring groove section 34 of the cap main unit 31 is among the holes 33a. In this configuration, exposed sections 41a of the linear members 41 can be obtained by inserting the linear member 41 into each hole 33a repeatedly, that is, repeating insertion of the linear member 41 alternately into a first one of the first holes 33a from outward to inward, into a second one of the holes 33a from inward to outward, into a third one of the holes 33a from outward to inward, and into a fourth one of the holes 33a from inward to outward, so that the linear member 41 in a deployed state form a substantial rectangular wave form. The exposed sections 41a of the linear members work as an incision knife when a high-frequency electric current is supplied to the linear member 41.

The endoscopic incision system according to the third embodiment facilitates supplying of the high-frequency electric current to the exposed sections 41a since the linear member 41 in one piece forms the exposed sections 41a that work as the incision knife. In addition, tensions applied to the exposed sections 41a can be substantially equal since tensions applied to the exposed sections 41a have no differences. An inadvertent event that one piece of linear member or a plurality of linear members are removed can be avoided since the linear members are connected with each other. In addition, the linear member 41 in full length can endure a load onto the exposed section 41a even if it is applied at one point; therefore, an effect that can increase tolerance for deformability of the exposed section.

Fourth Embodiment

Figure 6:
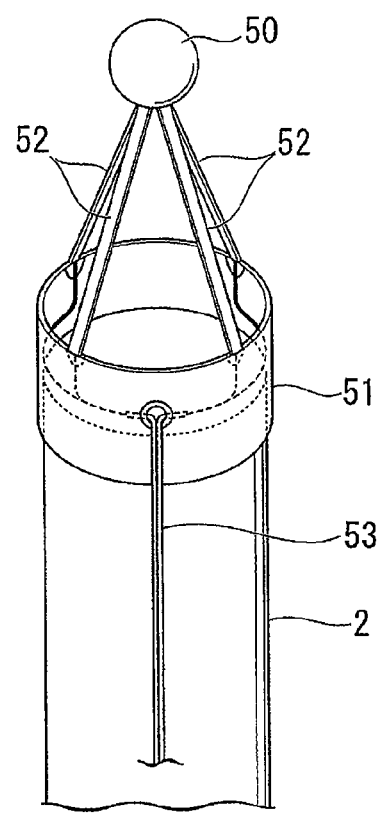
FIG. 6 is an isometric view showing the main part of the endoscopic incision system according to a fourth embodiment of the present invention.

FIG. 6 is an isometric view showing the main part of an endoscopic incision system according to a fourth embodiment of the present invention.

The fourth embodiment is characterized in that, a round-tip bougie section 50 is provided to the distal end of the overtube 2; and in that a high-frequency electric current is supplied through an energization wire 53 to a linear member 52 that is placed between the bougie section 50 and a radially-expanded section 51 provided to the distal end of the overtube 2.

It should be noted that configurations that are similar to those of the previously explained first embodiment will be assigned the same numeric symbols and redundant explanations thereof will be omitted.

The bougie section 50 used in the fourth embodiment has a round-tip shape and is small. In addition, the present embodiment does not have support columns for supporting the bougie section 50. Therefore, it is possible to obtain a more desirable visual field when observing ahead of the endoscope than in a case using the radially-expanded dome-shaped bougie section 33 used in the second or third embodiment. In addition, it is possible to obtain an opening section in front thereof since the aforementioned bougie section 50 has a radially-reduced diameter of round-tip shape in the aforementioned case. Using this expanded opening section enables treatment by projecting an instrument distally from the channel of the insertion section of an endoscope.

It should be noted that the round-tip bougie section 50 used in the aforementioned case may be, for example, a ball made of ceramics or polycarbonate material and having a diameter of substantially 2 to 10 mm.

Figure 7:
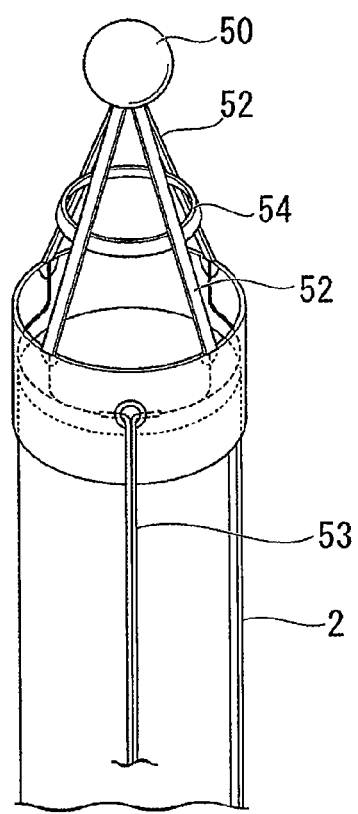
FIG. 7 is an isometric view showing a modified example of the fourth embodiment.

It should be noted that, the present invention is not limited to the example shown in the fourth embodiment using four pieces of the linear members 52 as shown in FIG. 6, and that three pieces of the linear members 52 or five or more pieces of the linear members 52 may be used. Also, as shown in FIG. 7, intermediate sections of the linear members 52 may be connected by a reinforcement member 54 having a ring shape for collectively enhancing the stiffness of the linear members.

It should be noted that the incision section used in the aforementioned embodiments for incising a living tissue provided between the tube main unit or the cap main unit and the bougie section will not be limited to a linear member, and that, for example, a bar-shaped member or a sheet member may be used.

In addition, the component provided to the distal end of the cap or the overtube may not be a dome-shaped or round-tip bougie section as shown in the aforementioned embodiments. A configuration using a distal end section not having a function of expanding the space in the living tissue may be used.

In addition, the present invention is not limited to the configurations shown in the second to fourth embodiments in which a living tissue is incised by supplying a high-frequency electric current to the linear members. In another configuration, a living tissue may be incised not by supplying a high-frequency electric current to an incision sections such as linear members or sheet members provided around the outer periphery of the cap 30 or ahead of the overtube 2 but by using the incision sections as cutting edges.

In addition, a recessed section formed between the bougie section 33 and the radially-expanded section 35 in the second or the third embodiment may not be the ring groove section 34. That is, to say briefly, the recessed section may be a hole as long as it has at least a recessed section or a hollow section inward relative to the incision section.

The present invention is not limited to the above descriptions but is limited only by the appended claims.

What is claimed is:

1. An endoscopic incision system comprising:
    an endoscope;
    a cylindrical member that covers at least a distal end of an insertion section of the endoscope;
    an incision section that incises a living tissue, the incision section being provided to a distal end of the cylindrical member and being capable of being exposed from the distal end of the cylindrical member distally, the incision section includes a plurality of sheet members; and
    one of a dome-shaped or round-tip bougie section that is provided in a center of the distal end of the cylindrical member;

a reinforcement member having a ring shape connected to an intermediate section of each of the plurality of sheet members;

wherein the a plurality of sheet members expand outwardly in a radial direction of the cylindrical member while proximally extending from the bougie section, the plurality of sheet members being configured to provide the incising of living tissue with rotation of the cylindrical member, with a plurality of openings being provided between the plurality of sheet members and the reinforcement member configured to prevent the plurality of sheet members from twisting or bending, and the bougie section is formed of an insulation material and is supported by the incision section.

2. The endoscopic incision system according to claim 1, further comprising a hollow section that is provided inwardly relative to the incision section and that is continued outwardly relative to the incision section through the plurality of the openings.

3. The endoscopic incision system according to claim 2, wherein the cylindrical member is an overtube covering the insertion section of the endoscope.

4. The endoscopic incision system according to claim 1, wherein the bougie section is a transparent insulator member.

* * * * *